United States Patent
Umemura et al.

(10) Patent No.: US 7,278,968 B2
(45) Date of Patent: Oct. 9, 2007

(54) ULTRASONOGRAPH

(75) Inventors: Shin-ichiro Umemura, Hachiouji (JP); Ken-ichi Kawabata, Kodaira (JP)

(73) Assignee: Hitachi Medical Corporation, Tokyo (JP)

( * ) Notice: Subject to any disclaimer, the term of this patent is extended or adjusted under 35 U.S.C. 154(b) by 437 days.

(21) Appl. No.: 10/466,630

(22) PCT Filed: Feb. 6, 2002

(86) PCT No.: PCT/JP02/00945

§ 371 (c)(1),
(2), (4) Date: Jul. 18, 2003

(87) PCT Pub. No.: WO03/026508

PCT Pub. Date: Apr. 3, 2003

(65) Prior Publication Data

US 2004/0152985 A1     Aug. 5, 2004

(30) Foreign Application Priority Data

Sep. 20, 2001    (JP) .............................. 2001-286315

(51) Int. Cl.
*A61B 8/06* (2006.01)
(52) U.S. Cl. ..................................................... 600/458
(58) Field of Classification Search ........ 600/443–447, 600/454–456, 458; 128/916
See application file for complete search history.

(56) References Cited

U.S. PATENT DOCUMENTS

| | | | |
|---|---|---|---|
| 5,523,058 A * | 6/1996 | Umemura et al. ........... 422/128 |
| 5,558,092 A * | 9/1996 | Unger et al. ................. 600/439 |
| 5,957,845 A * | 9/1999 | Holley et al. ................ 600/440 |
| 6,398,735 B1 * | 6/2002 | Clark ........................... 600/458 |
| 6,656,123 B2 * | 12/2003 | Jensen et al. ................ 600/458 |
| 6,899,679 B2 * | 5/2005 | Kawagishi et al. .......... 600/443 |
| 6,905,467 B2 * | 6/2005 | Bradley et al. .............. 600/443 |

* cited by examiner

*Primary Examiner*—Francis J. Jaworski
(74) *Attorney, Agent, or Firm*—Antonelli, Terry, Stout & Kraus, LLP.

(57) ABSTRACT

An ultrasonograph is provided wherein the decrease of the density of the stabilized microbubble contrast agent in a desired body target area can be inhibited, radiating ultrasonic energy required for satisfactory signal-to-noise ratio and sufficient frame rate, where an ultrasonic probe transmits an ultrasonic pulse acquired by superimposing higher harmonics including a second harmonic of the fundamental onto the fundamental wave, such as a maximum positive pressure enhanced waveform or a maximum negative pressure enhanced waveform, or an acoustic pressure rise enhanced waveform or an acoustic pressure fall enhanced waveform.

7 Claims, 12 Drawing Sheets

ULTRASONOGRAPH

This application is a 371 of PCT/JP02/00945 filed Feb. 6, 2002.

TECHNICAL FIELD

The present invention relates to an ultrasonograph for obtaining an image of the inside of a living body by transmitting/receiving an ultrasonic wave to/from the living body.

BACKGROUND ART

An ultrasonograph that transmits/receives an pulsed ultrasound to/from a living body and senses the inside of the living body is widely used in medical diagnosis. In fields of X-ray and MRI out of image diagnostic modalities, a contrast agent has been used for imaging of a circulatory system.

In the meantime, in ultrasonic diagnosis, a contrast agent has been not widely used, however, in a few years, a contrast agent made of formulation consists of microbubbles several micrometers in size stabilized in several methods begins to be widely used. The principle of contrast enhancing utilizes that a microbubble the diameter of which is approximately 1 micron oscillates with large amplitude resonanting with an ultrasonic wave of several MHz used for ultrasonic diagnosis, and as a result, the contrast enhancement is achieved by the improved reflection of ultrasonic wave.

The property of a contrast agent for X-ray and MRI are not affected by an irradiated electromagnetic wave or magnetic fields for imaging. However, a contrast agent made of stabilized microbubble formulation is collapsed and eliminated by an ultrasonic wave radiated for imaging and the performance of contrast may severely decrease. This prevents imaging with ultrasound intense and frequent enough to obtain acceptable signal-to-noise ratio while obtaining steady contrast enhancing effects with microbubble based contrast agent.

On the contrary, the phenomenon that microbubble is collapsed by ultrasound can be utilized to eliminate contrast agent in the region of interest at desired time to re-initialize the conditions for contrast enhancement. This can be also regarded as an unique advantage of microbubble-based ultrasound contrast agent over contrast agents for X-ray and MRI.

Ultrasonic energy per unit time is widely used as the simplest index for expressing the magnitude of an ultrasonic wave and generally referred to as ultrasonic intensity. Besides, recently, for a physical index showing the possibility of cavitation by an ultrasonic wave in water or in a living body, a mechanical index (MI) defined as an expression MI=(maximum negative pressure)/(square root of mean frequency) has been widely used.

Then, in an ultrasonic diagnostic system based upon prior art, a mode for lowering the magnitude of an ultrasonic wave expressed in above indexes and the frequency of radiation is equipped used when the density of a contrast agent in a living body, for example, in a desired living area is not to be decreased. However, problems that signal-to-noise ratio is not enough, or the temporal changes of the region of interest cannot be monitored arise due to low intensity of ultrasonic wave, or low frequency of radiation, respectively.

In the meantime, when re-initialize the contrast enhancement conditions by elimination of contrast agents in the region of interest in living body, achieved by exposing higher intensity ultrasound when required, ultrasound intensity and mechanical index should be in the safety range. This causes a problem that the re-initialization cannot be achieved within a period short enough to meet the requests of doctors or other medical staffs who operate the diagnostic system in the prior art.

For prior art related to the latter problem, technique for causing cavitation at low ultrasonic intensity in water or in a living body by a device that the second harmonic is superimposed on a fundamental wave and it is radiated and promoting acoustic chemical reaction is described in Journal of Chemical Physics (Vol. 100, p. 18784 to p. 18789), in Journal of Acoustical Society of America (Vol. 101, p. 569 to p. 577), in IEEE Transactions on Ultrasonics, Ferroelectrics, and Frequency Control (Vol. 43, p. 1054 to p. 1062).

However, it is technique for promoting cavitation and to solve the latter problem, a method of relating the promotion of cavitation to the breaking of a stabilized microbubble and methodology are required.

DISCLOSURE OF THE INVENTION

The invention is made in view of such a situation and the object is to provide an ultrasonograph wherein first, the decrease of the density of a stabilized microbubble contrast agent in a desired living area can be inhibited, radiating ultrasonic energy required to acquire satisfactory image signal-to-noise ratio and a sufficient frame rate and second, the stabilized microbubble contrast agent in the desired living area can be efficiently eliminated if necessary, inhibiting the intensity of an ultrasonic wave and a mechanical index within a limit for safety.

It is indicated in the above mentioned published documents that the action of an ultrasonic wave upon a contrast agent such as a microbubble introduced into water or the inside of a living body can be greatly changed even if the intensity of the ultrasonic wave is equal when higher harmonics are superimposed on a fundamental wave and it is radiated.

Thus, the application of this idea to an ultrasonic pulse used for transmission when an image is obtained is tried. When the phase is controlled in superimposing the second harmonic on a fundamental wave, acoustic pressure waveforms shown in FIGS. 5 to 8 described later detailedly, a maximum positive pressure enhanced waveform shown in FIG. 5 in which the peak value on the side of positive acoustic pressure of maximum amplitude is enhanced, that is, is larger than the peak value on the side of negative acoustic pressure, a maximum negative pressure enhanced waveform shown in FIG. 6 in which the peak value on the side of negative acoustic pressure of maximum amplitude is enhanced, that is, is larger than the peak value on the side of positive acoustic pressure, an acoustic pressure rise enhanced waveform shown in FIG. 7 and also called N wave in which the leading edge of an ultrasonic acoustic pressure waveform is sharper than the trailing edge and an acoustic pressure fall enhanced waveform shown in FIG. 8 and also called reverse N wave in which the trailing edge of an ultrasonic acoustic pressure waveform is sharper than the leading edge can be produced.

FIG. 1 shows the result of theoretically predicting its behavior when a microbubble is exposed to acoustic pressure having such a waveform by numerical calculation and comparing with the total ultrasonic energy of a fundamental wave and a second higher harmonic common. In FIG. 1, a thick solid line denotes a case of the maximum positive pressure enhanced waveform, a thick dotted line denotes a case of the maximum negative pressure enhanced waveform, a thin solid line denotes a case of the acoustic pressure rise enhanced waveform and a thin dotted line denotes a case of the acoustic pressure fall enhanced waveform.

FIG. 1 shows that in the acoustic pressure fall enhanced waveform, the maximum surface area of an oscillating microbubble is maximum and conversely, for an area in which the intensity of an ultrasonic wave is relatively low, in the acoustic pressure rise enhanced waveform or the maximum positive pressure enhanced waveform, the maximum surface area of the oscillating microbubble is minimum.

As in most stabilized microbubble formulation, a microbubble is stabilized by arranging a surface active agent or a similar substance on the surface of the microbubble, the maximum surface area of the oscillating microbubble is considered to be a physical index of the unstableness of the microbubble by acoustic pressure. That is, it is considered that under a condition that the total ultrasonic energy of a fundamental wave component and the second harmonic component is fixed, the acoustic pressure rise enhanced waveform or the maximum positive pressure enhanced waveform is suitable when an image is obtained, inhibiting the decrease of the density of a stabilized microbubble contrast agent in a desired living area, and to efficiently eliminate the stabilized microbubble contrast agent in the desired living area, the acoustic pressure fall enhanced waveform is suitable.

FIG. 2 shows the result of comparing each waveform in relation to the maximum surface area of an oscillated microbubble with a mechanical index common. A thick full line, a thick dotted line, a thin full line and a thin dotted line in FIG. 2 are similar to those in FIG. 1. In this case, the maximum surface area of an oscillating microbubble is maximum in the maximum positive pressure enhanced waveform. Therefore, it is considered that to efficiently eliminate a stabilized microbubble contrast agent in a desired living area under a condition that a mechanical index is fixed, the maximum positive pressure enhanced waveform is suitable.

As described above, the problems are solved in the invention by producing a waveform suitable for inhibiting the decrease of the density of the stabilized microbubble contrast agent in a desired living area by superimposing higher harmonics on a fundamental wave and controlling the phase of both and conversely, a waveform suitable for efficiently decreasing and suitably using any of them if necessary.

Thereby, an ultrasonograph according to the invention is based upon an ultrasonic diagnostic system for imaging of the inside of a living body by transmitting/receiving an ultrasonic wave to/from the living body into which a contrast agent is introduced using an ultrasonic probe and is characterized in that the ultrasonic probe is configured so that it transmits an ultrasonic pulse in which higher harmonics including at least a second harmonic of a fundamental wave is superimposed on the fundamental wave.

Besides, the invention is based upon the configuration and is characterized in that an ultrasonic pulse transmitted from the ultrasonic probe includes the acoustic pressure fall enhanced waveform in which the trailing edge of the ultrasonic waveform is sharper than the leading edge.

Besides, the invention is based upon the configuration and is characterized in that an ultrasonic pulse transmitted from the ultrasonic probe includes the maximum positive pressure enhanced waveform in which the peak value on the side of positive acoustic pressure of maximum amplitude is larger than the peak value on the side of negative acoustic pressure.

Besides, the invention is based upon the configuration and is characterized in that the acoustic pressure fall enhanced waveform and the maximum positive pressure enhanced waveform can be switched according to a transmission mode.

Besides, the invention is based upon the configuration and is characterized in that an ultrasonic image obtained using an ultrasonic pulse having the acoustic pressure fall enhanced waveform or the maximum positive pressure enhanced waveform is displayed.

Besides, the invention is based upon the configuration and is characterized in that the contrast agent includes a microbubble and the mean frequency of the fundamental wave is set to the resonance frequency of the microbubble.

Besides, the invention is based upon the configuration and is characterized in that the ultrasonic pulse has a waveform acquired by superimposing second harmonics the phase of which is shifted by $\pi/2$ from the fundamental wave at a point that crosses zero on the fundamental wave.

Besides, the invention is based upon the configuration and is characterized in that the ultrasonic pulse has a waveform acquired by superimposing second harmonics the phase of which is equal to that of the fundamental wave at a point that crosses zero on the fundamental wave.

Further, the invention is based upon the configuration and is characterized in that for the ultrasonic pulse, a maximum positive pressure enhanced waveform in which the peak value on the side of positive acoustic pressure of maximum amplitude is larger than the peak value on the side of negative acoustic pressure, a maximum negative pressure enhanced waveform in which the peak value on the side of negative acoustic pressure of maximum amplitude is larger than the peak value on the side of positive acoustic pressure, an acoustic pressure rise enhanced waveform in which the leading edge of an ultrasonic waveform is sharper than the trailing edge and an acoustic pressure fall enhanced waveform in which the trailing edge of the ultrasonic wave is sharper than the leading edge are recorded beforehand and one waveform of them is selected and used.

Furthermore, the invention is based upon the configuration and is characterized in that a first mode in which an ultrasonic pulse having the acoustic pressure rise enhanced waveform or the maximum positive pressure enhanced waveform as a principal component is transmitted and a second mode in which an ultrasonic pulse having the acoustic pressure fall enhanced waveform or the maximum positive pressure enhanced waveform as a principal component is transmitted can be switched.

BEST EMBODIMENTS FOR EMBODYING THE INVENTION

Figure 1:
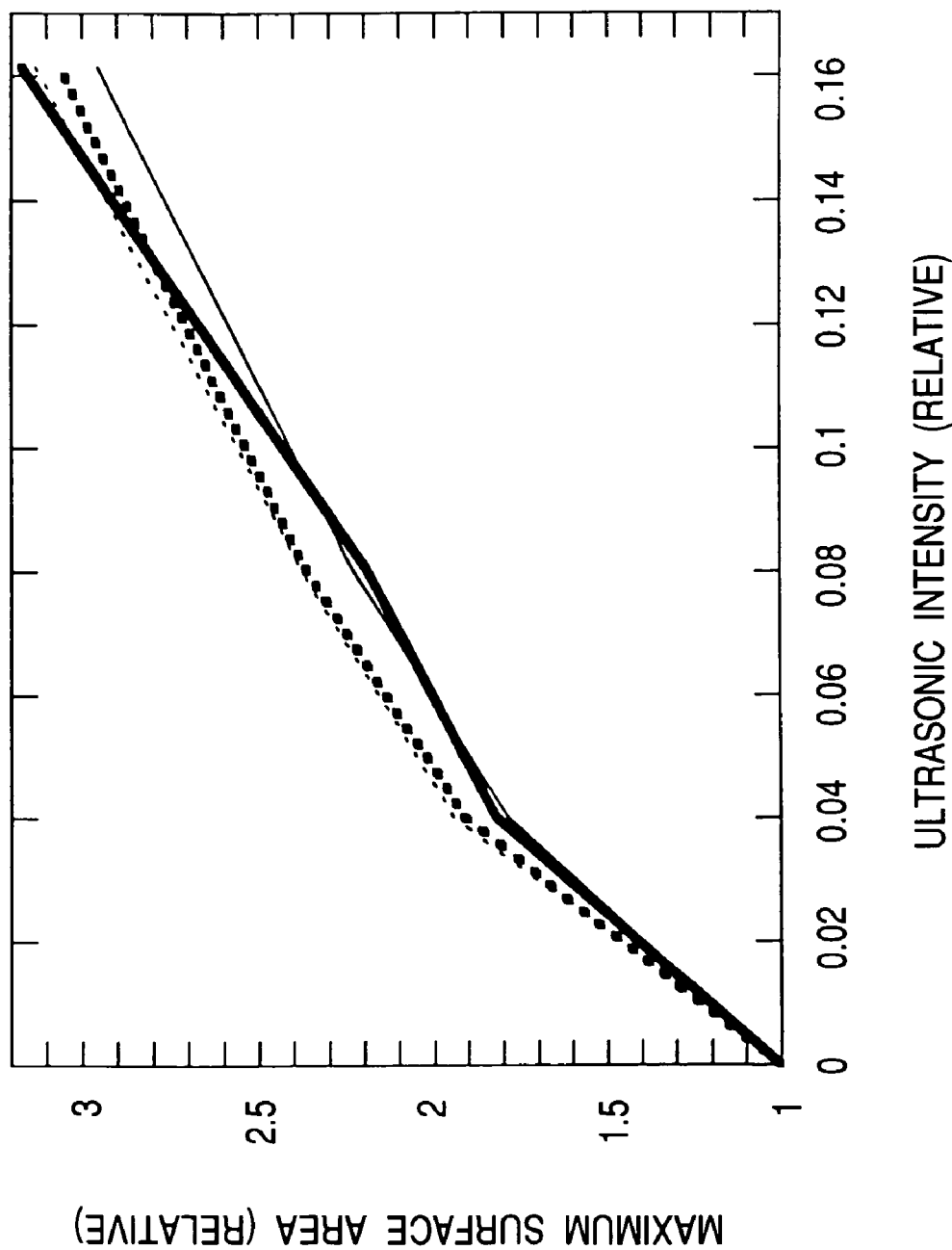
FIG. 1 shows the maximum surface area of an oscillating microbubble compared with the total ultrasonic energy of a fundamental wave and a second harmonic common.
Figure 2:
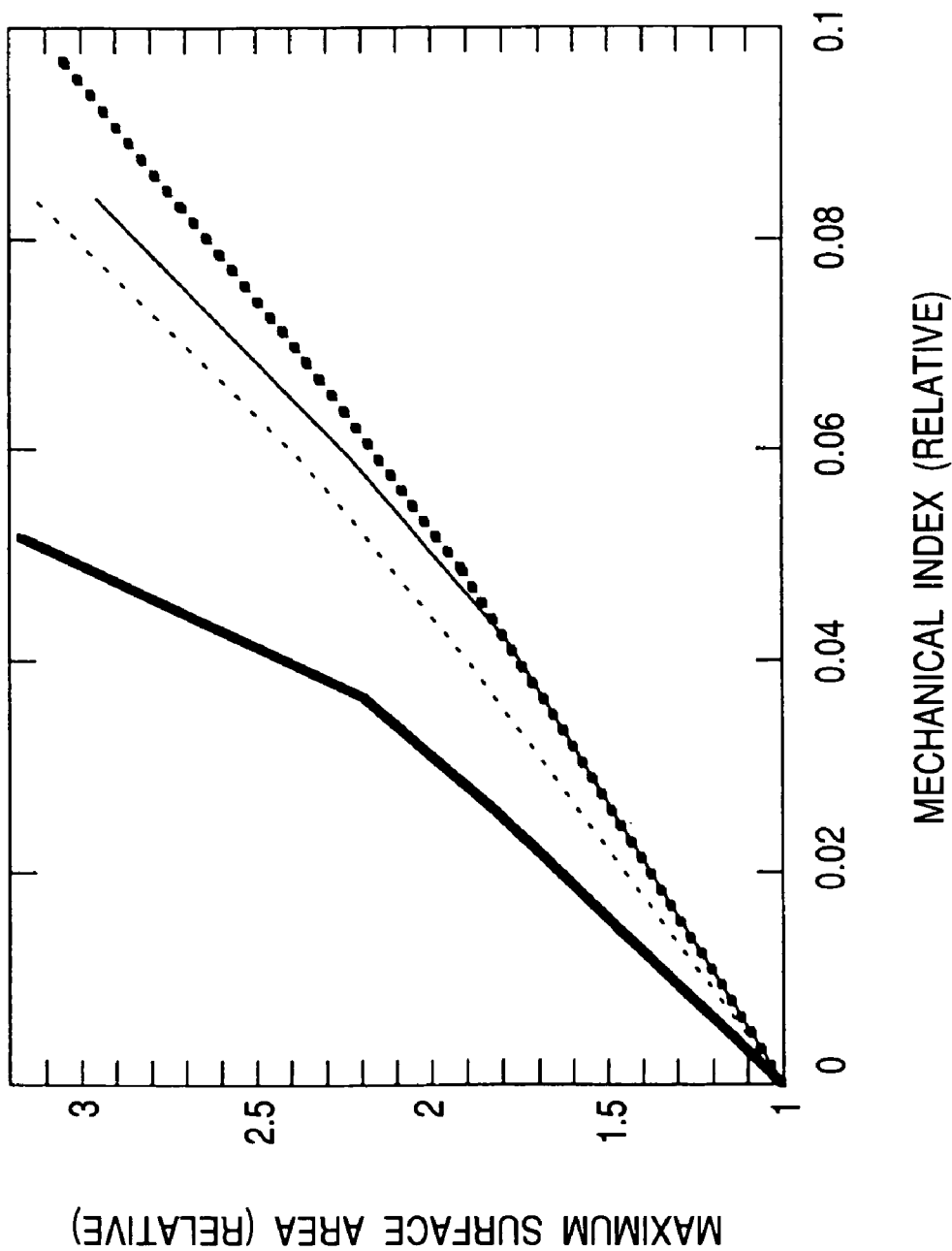
FIG. 2 shows the maximum surface area of an oscillated microbubble compared with a mechanical index common.

Referring to the drawings, embodiments of the invention will be described below.

Figure 3:
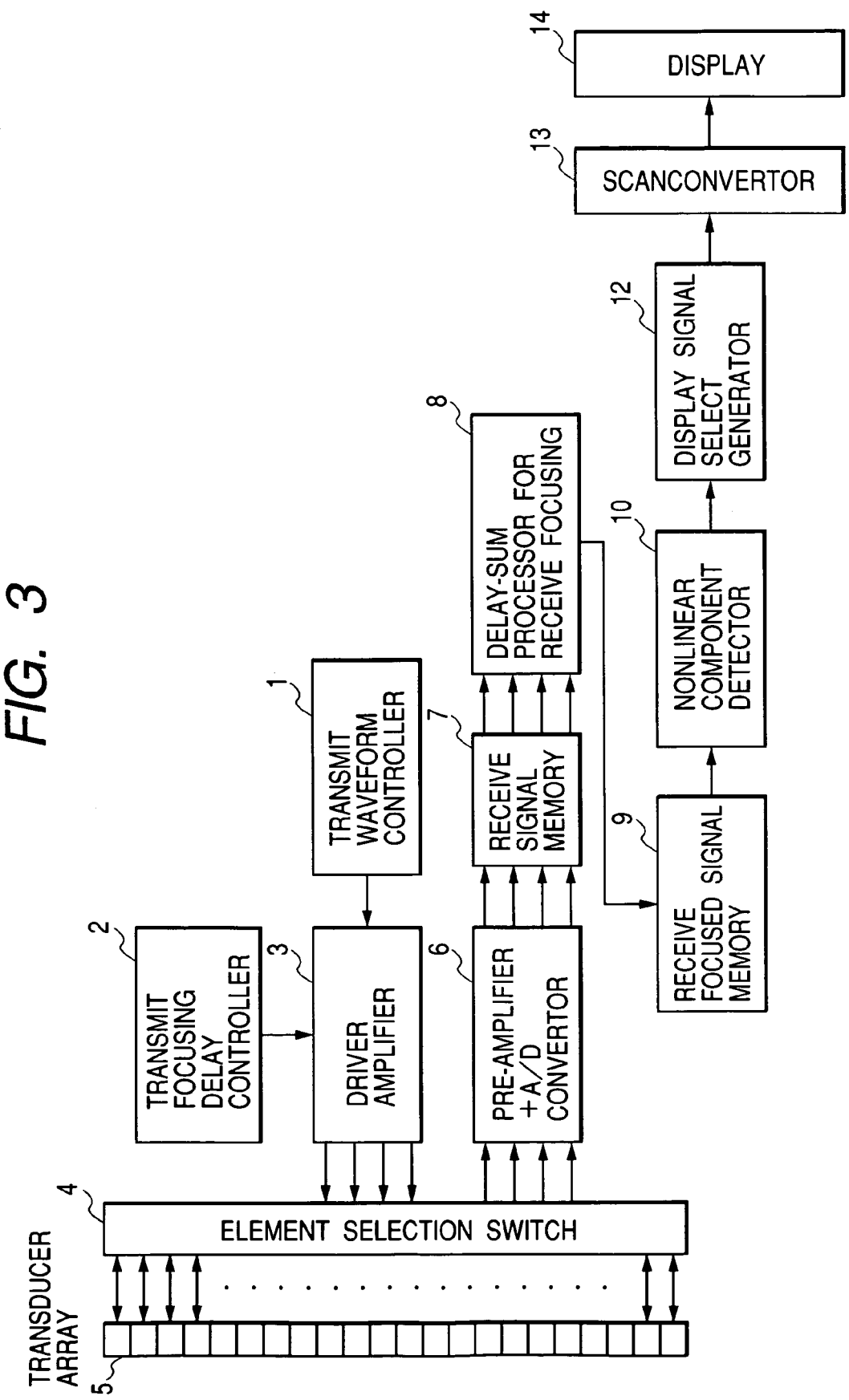
FIG. 3 is a block diagram for explaining the configuration of one embodiment of the invention.
Figure 4:
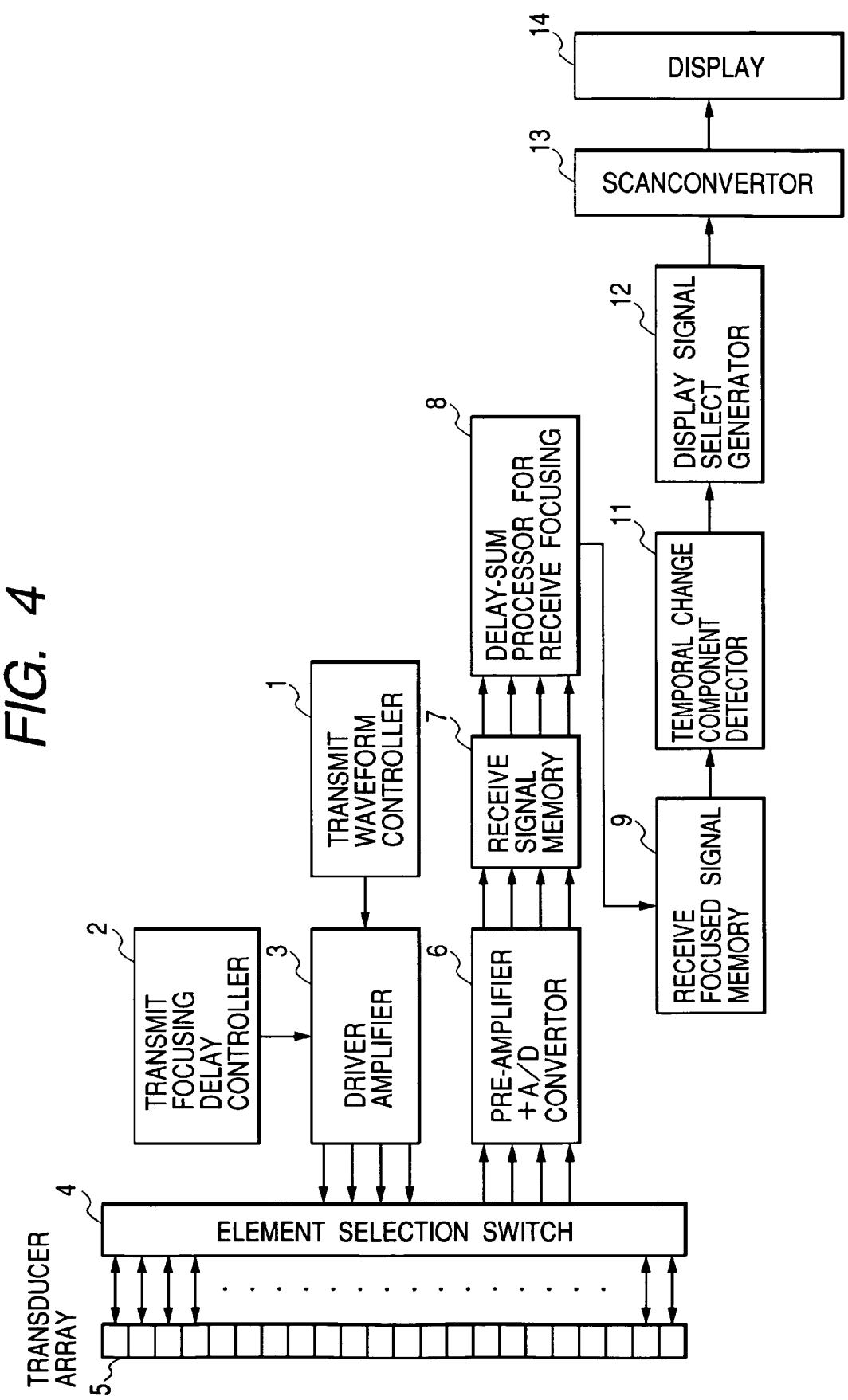
FIG. 4 is a block diagram for explaining the configuration of another embodiment of the invention.

FIGS. 3 and 4 are block diagrams showing the typical configuration of an ultrasonograph acquired by applying the invention to an ultrasonic diagnostic system based upon a pulse-echo method.

Figure 5:
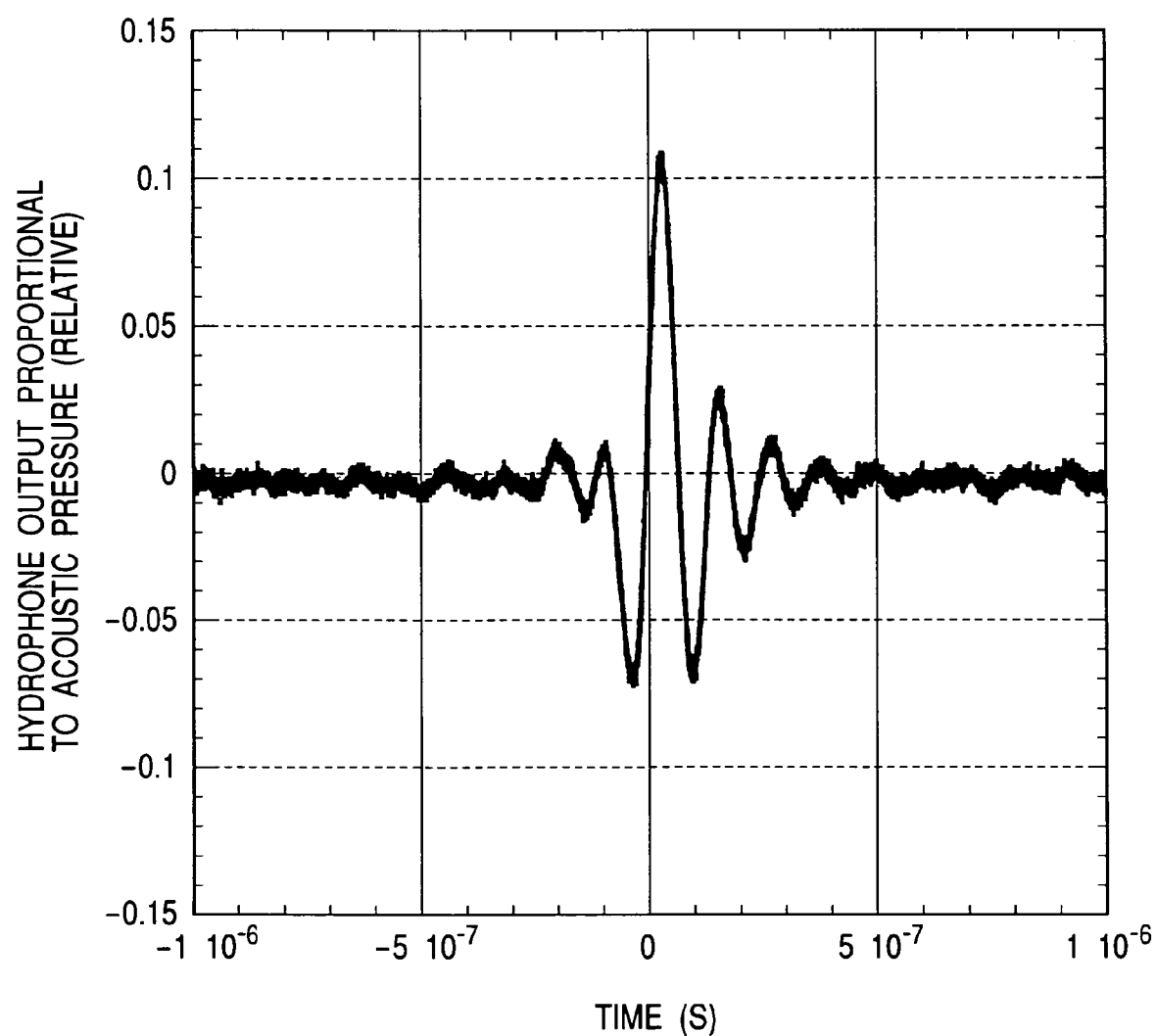
FIG. 5 shows a transmitted wave acoustic pressure waveform (1) measured by a needle like hydrophone in the vicinity of a probe of an ultrasonograph according to the invention.
Figure 6:
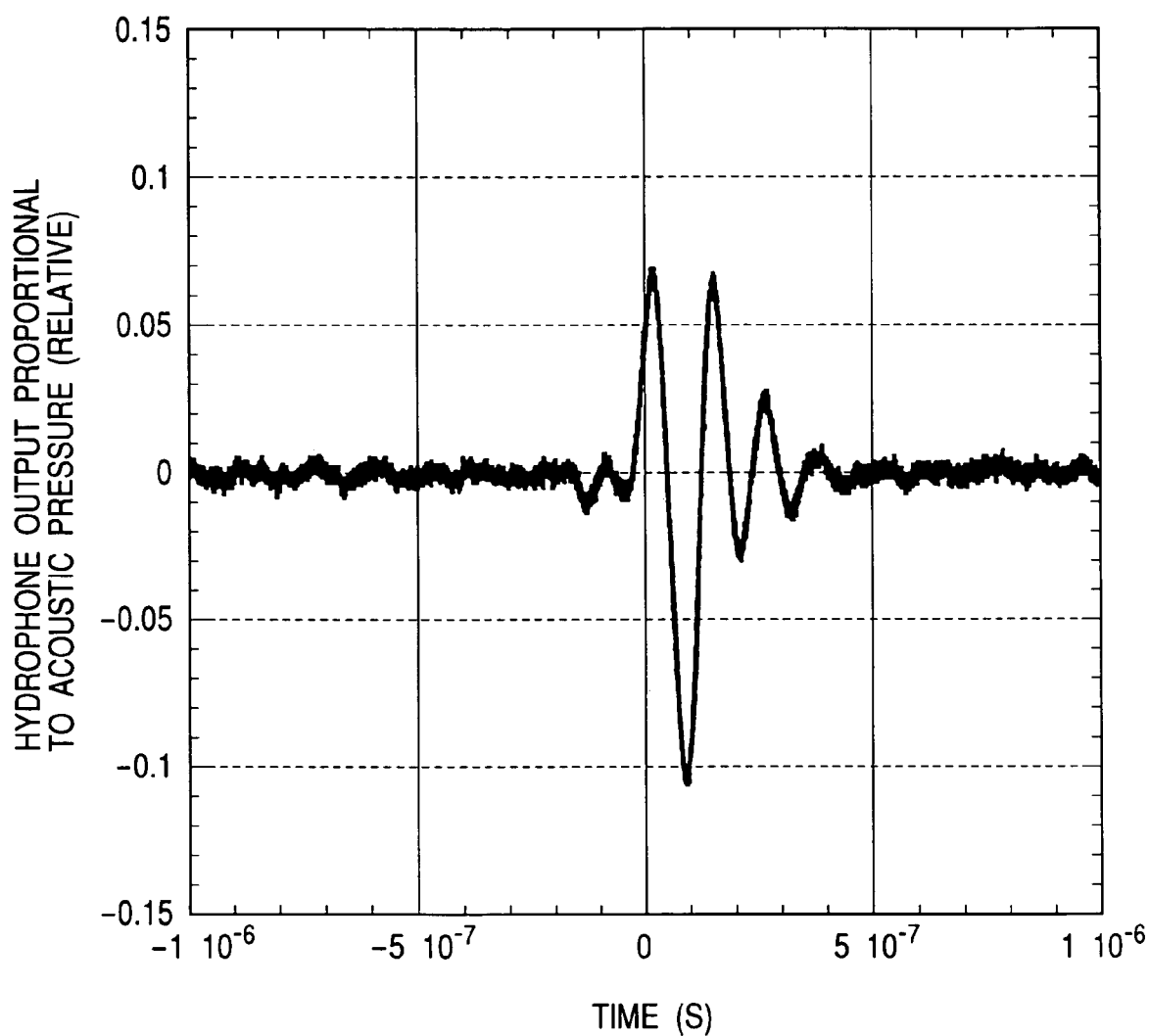
FIG. 6 shows a transmitted wave acoustic pressure waveform (2) measured by the needle like hydrophone in the vicinity of the probe of the ultrasonograph according to the invention.
Figure 7:
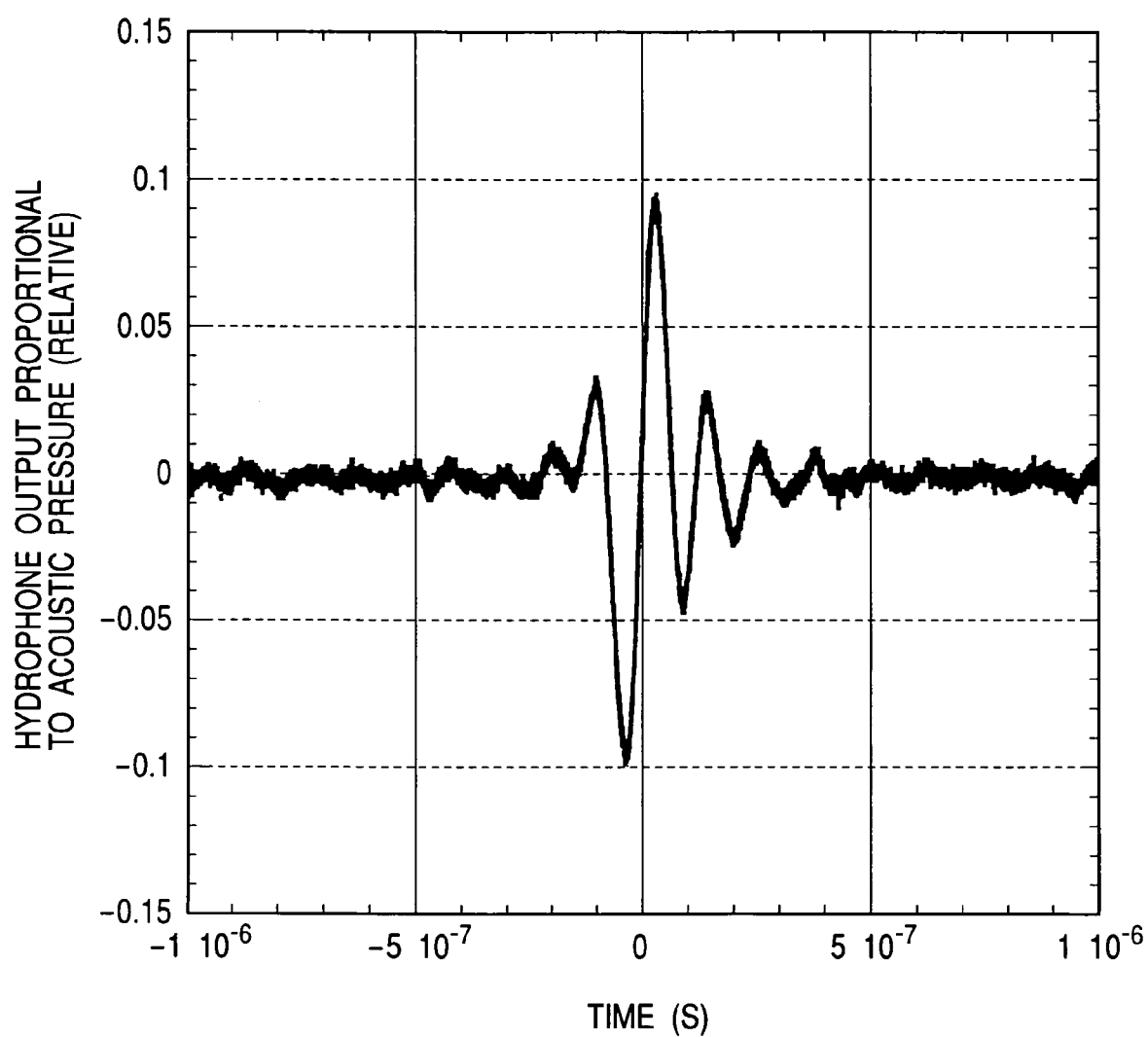
FIG. 7 shows a transmitted wave acoustic pressure waveform (3) measured by the needle like hydrophone in the vicinity of the probe of the ultrasonograph according to the invention.
Figure 8:
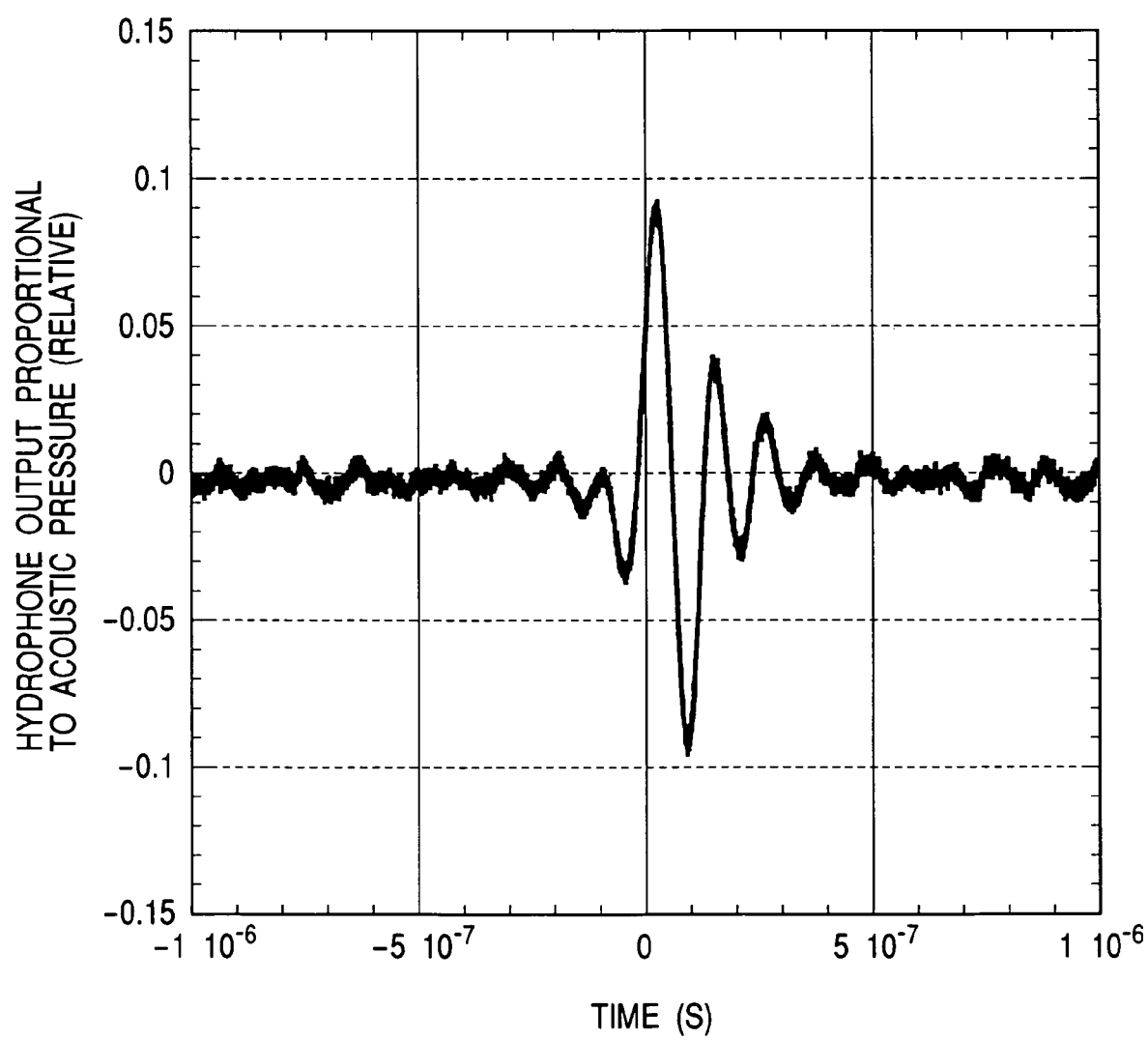
FIG. 8 shows a transmitted wave acoustic pressure waveform (4) measured by the needle like hydrophone in the vicinity of the probe of the ultrasonograph according to the invention.
Figure 9:
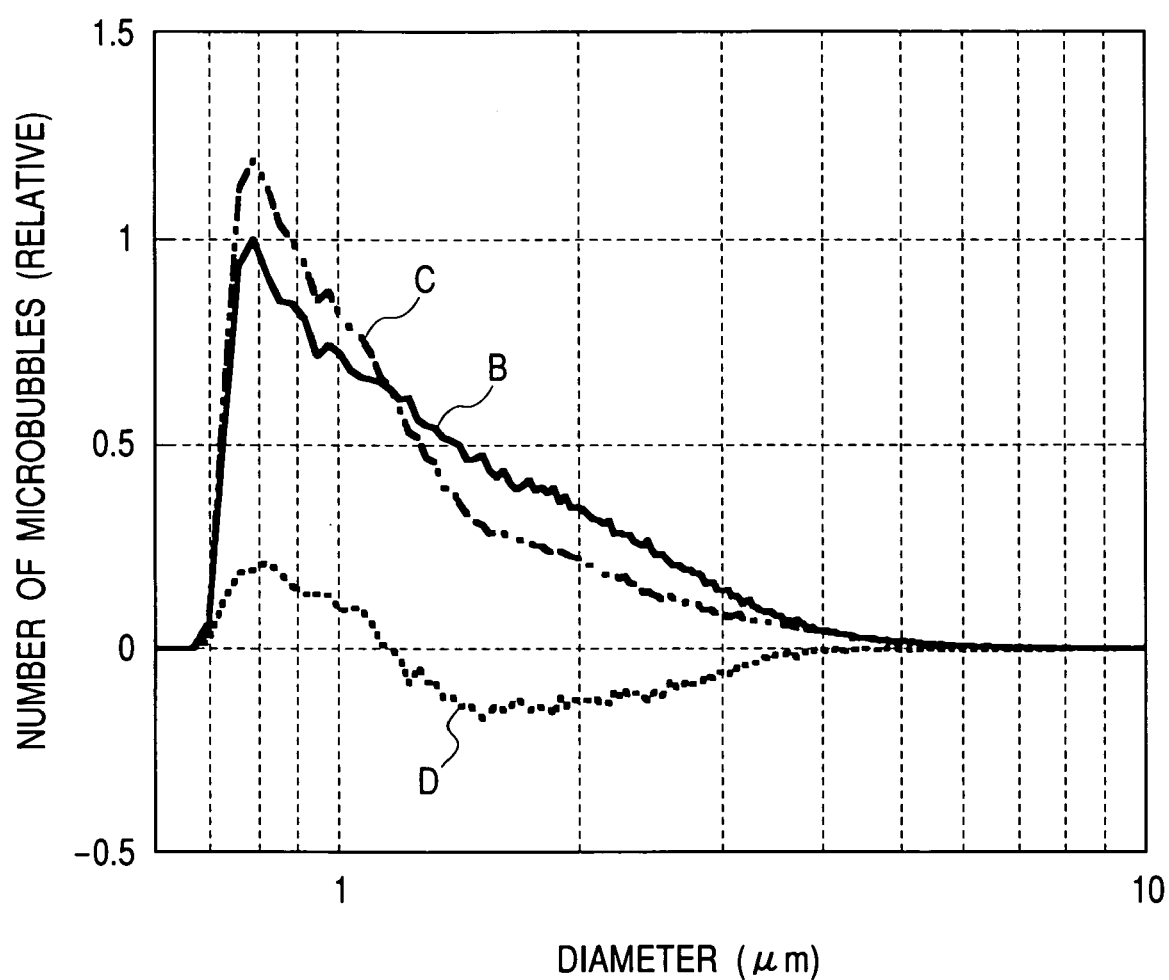
FIG. 9 shows the result (1) of measuring the distribution of the particle diameter of a stabilized microbubble before and after the radiation of an ultrasonic wave by the ultrasonograph according to the invention.
Figure 10:
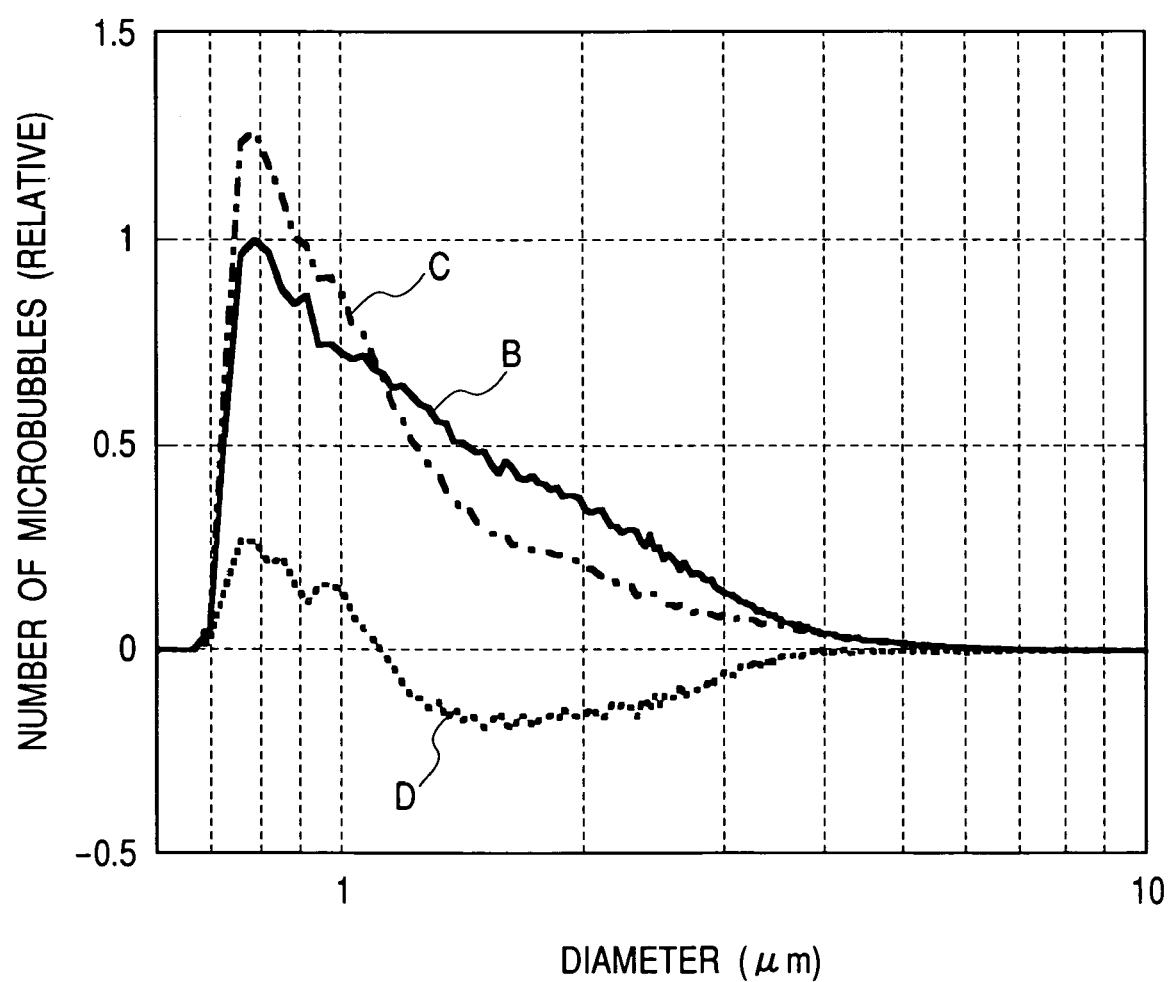
FIG. 10 shows the result (2) of measuring the distribution of the particle diameter of a stabilized microbubble before and after the radiation of an ultrasonic wave by the ultrasonograph according to the invention.
Figure 11:
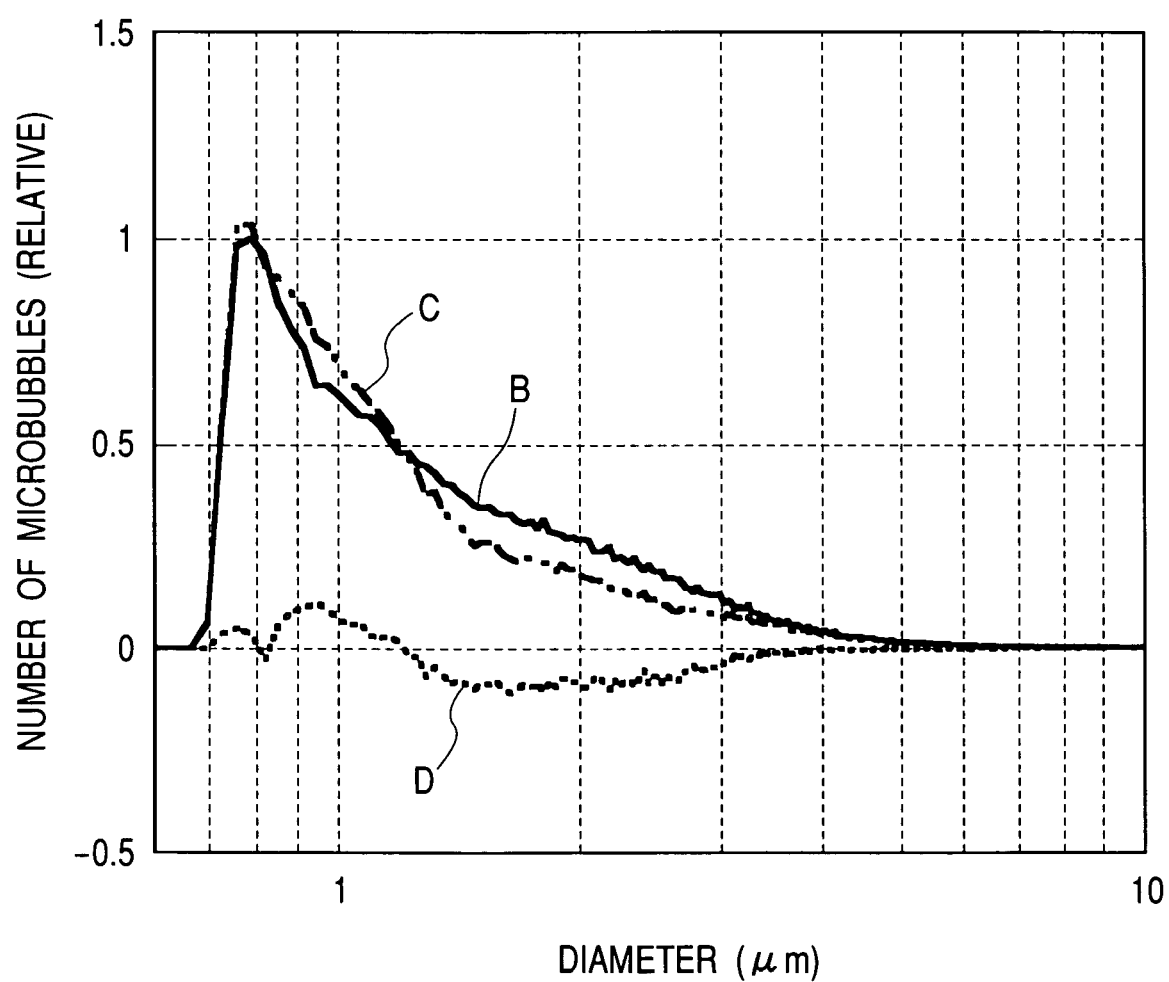
FIG. 11 shows the result (3) of measuring the distribution of the particle diameter of a stabilized microbubble before and after the radiation of an ultrasonic wave by the ultrasonograph according to the invention.
Figure 12:
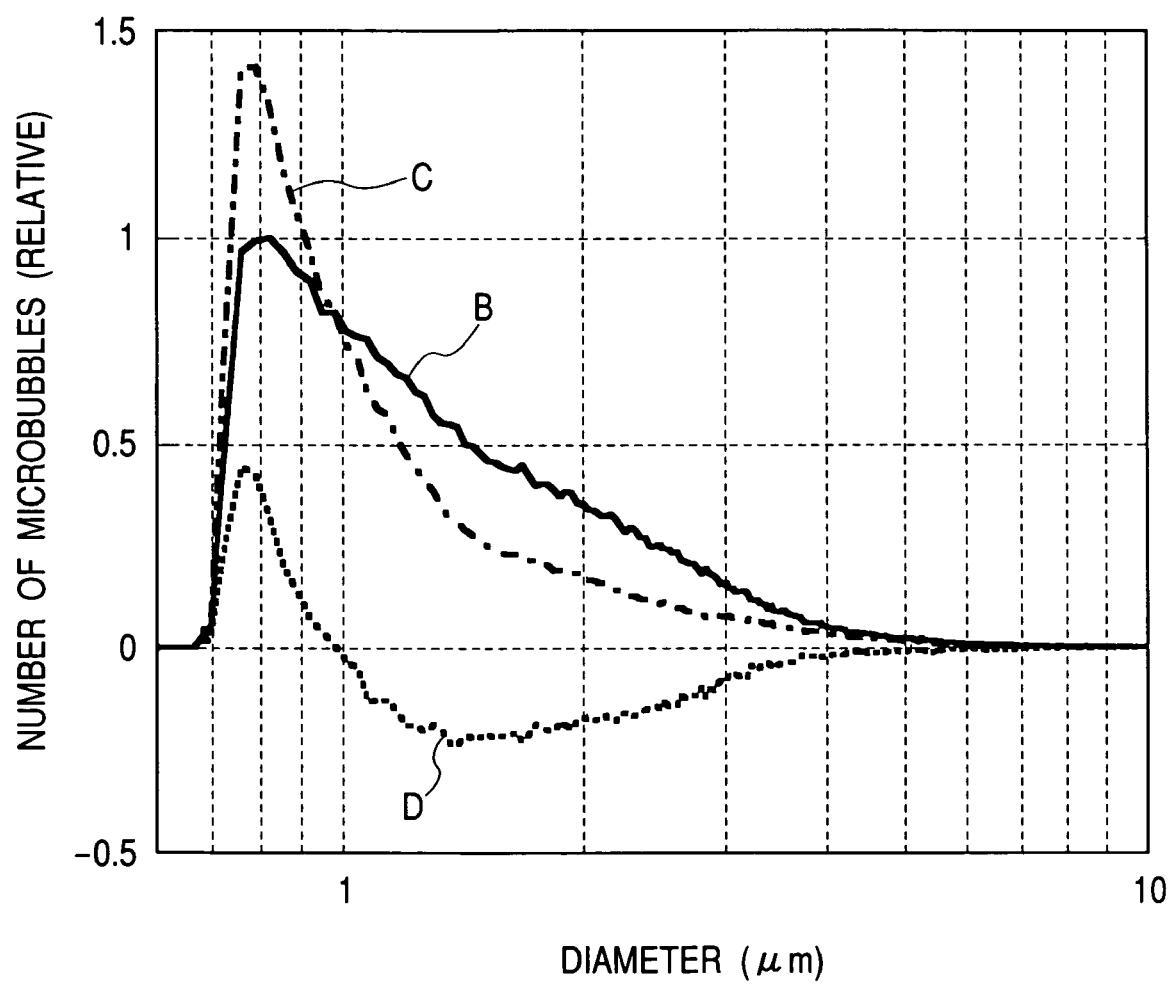
FIG. 12 shows the result (4) of measuring the distribution of the particle diameter of a stabilized microbubble before and after the radiation of an ultrasonic wave by the ultrasonograph according to the invention.

In a transmit waveform controller 1, a transmit waveform is selected out of plural waveforms beforehand recorded such as acoustic pressure waveforms shown in FIGS. 5 to 8 as examples, to describe in detail, a maximum positive-pressure enhanced waveform shown in FIG. 5 in which the peak value on the side of positive acoustic pressure of maximum amplitude is enhanced, that is, is made larger than the peak value on the side of negative acoustic pressure, a maximum negative-pressure enhanced waveform shown in FIG. 6 in which the peak value on the side of the negative acoustic pressure of maximum amplitude is enhanced, that is, is made larger than the peak value on the side of the positive acoustic pressure, an acoustic pressure rise enhanced waveform shown in FIG. 7 in which the leading edge of an ultrasonic acoustic pressure waveform is sharper than the trailing edge and an acoustic pressure fall enhanced waveform shown in FIG. 8 in which the trailing edge of an ultrasonic acoustic pressure waveform is sharper than the leading edge, controlled amplitude is applied to the transmit waveform and it is applied to a drive amplifier 3. To apply directivity to a transmitted wave, delay is applied to a transmitted signal to be applied to each element selected by an element selecting switch 4 out of elements forming a transducer array (an ultrasonic probe) 5 and convergence effect is required to be acquired, and a transmitted wave convergence/delay control unit 2 controls the delay.

A directive ultrasonic pulse transmitted to a living body from the transducer array 5 as described above is reflected on a tissue of the living body and a contrast agent, a part returns to the transducer array 5 again and is received by each element forming it. After each signal of elements selected by the element selecting switch 4 out of received signals is amplified by a preamplifier 6, it is converted from analog to digital (A/D) and is once stored in a received wave memory 7.

More detailedly, it is general that after each signal described above is made to pass a TGC amplifier controlled so that an amplification factor is gradually increased depending upon time elapsed since transmission immediately after the preamplifier 6, it is converted from analog to digital. This is a process for keeping the amplitude of a signal at the entrance of an A/D converter in a fixed range to compensate the reduction of the amplitude of the received signal substantially in proportion to the time elapsed since transmission corresponding to the attenuation of an ultrasonic wave transmitted in the living body substantially in proportion to transmitted distance. Hereby, the deterioration of a signal dynamic range caused by the quantization of amplitude in analog-to-digital conversion is prevented. Further, in addition to this, aliasing caused by the quantization of a time base in the analog-to-digital conversion can be prevented by installing a band limit filter before the A/D converter.

To acquire the directivity of a received wave, after delay of one type according to the position of each element is once applied to a signal received by each element and stored in the memory 7, the signals are added and convergence effect is required to be acquired. A received wave convergence/delay adding unit 8 executes the processing. An optimum value of delay time to be applied to a signal of each element is varied depending upon the focal length of a received wave. Besides, an optimum value of the focal length of a received wave for acquiring a satisfactory pulse echo image is made longer in proportion to time elapsed since transmission and acoustic velocity. Therefore, it is desirable that a receiving method that delay time to be applied to a signal of each element is varied according to time elapsed since transmission is used. This method can be relatively easily realized by control in reading or writing in the configurations shown in FIGS. 3 and 4 that a signal received by each element is once written to the memory, is read again and the signals are added.

In B mode of a general ultrasonic diagnostic system, the amplitude is acquired based upon a signal acquired by applying delay for converging a received wave in a detecting process and is logarithmically compressed to be a display signal. A display signal selective creation unit 12 shown in the drawings executes this processing, a scan converter 13 converts it to a two-dimensional image or a three-dimensional image according to circumstances and a display 14 displays it on CRT or a liquid crystal display according to circumstances.

Besides, in a harmonic imaging method, a nonlinear component is extracted from a signal acquired by applying delay for converging a received wave and the similar processing is applied to the component to be a display signal. Hereby, a pulse echo image in which the distribution of a stabilized microbubble contrast agent the nonlinear reflectivity of which is large, compared with a living tissue is enhanced can be acquired. In the most basic method of the harmonic imaging method, higher harmonics generated by nonlinear effect are separated from a fundamental wave via a bandpass filter and are extracted. However, in the ultrasonograph according to the invention, as a harmonic component is included in a transmitted signal beforehand, the basic method in which a harmonic component separated via the bandpass filter is used for a nonlinear component cannot be used as it is.

For a nonlinear component extracting method that does not depend upon a bandpass filter, there are a pulse inversion method and an amplitude modulation method. FIG. 3 shows one embodiment of the invention in case these are applied.

In the amplitude modulation method, one acoustic pressure waveform acquired by superimposing higher harmonics on a fundamental wave and shown in FIGS. 5 to 8 as examples is selected, the amplitude is varied plurally and it is transmitted. To extract a nonlinear component, a principle that the amplitude of an echo linear component of a received wave is proportional to the amplitude of a transmitted wave, however, the amplitude of a nonlinear component is not proportional to the amplitude of the transmitted wave is used.

To explain a case that two amplitudes are used as an example, a linear component is eliminated by once recording a signal acquired by converging a received wave acquired by transmitting a signal of first amplitude A1 in a memory 9, multiplying a signal acquired by converging a received wave acquired by transmitting a signal of second amplitude A2 by A1/A2 and calculating difference between the multiplied signal and the signal recorded in the memory 9, and a nonlinear component is extracted. In a normal amplitude modulation method, A1 and A2 are positive real numbers.

In the meantime, in a pulse inversion method, a pair of real numbers the absolute values of which are equalized by inverting each sign as A1 and A2 is used. To explain acoustic pressure waveforms shown in FIGS. 5 to 8 as examples, a waveform the maximum positive pressure of which is enhanced and a waveform the maximum negative pressure of which is enhanced, and a waveform the rise of the acoustic pressure of which is enhanced and a waveform the fall of the acoustic pressure of which is enhanced have the relation of a pair of one and the other acquired by inverting one. To explain operation in this case, a linear component is eliminated by selecting one acoustic pressure waveform, once recording a signal acquired by converging a received wave acquired by transmitting the selected acoustic pressure waveform in the memory 9 and next adding a signal acquired by converging a received wave acquired by transmitting its inverted pulse waveform and the signal recorded in the memory 9 and a nonlinear component is extracted. A display signal is acquired by applying the processing described above to a signal acquired by executing such signal processing in a nonlinear component extraction unit 10.

The method of acquiring a pulse echo image by enhancing the distribution of the contrast agent utilizing a fact that the microbubble contrast agent has larger nonlinear reflectivity, compared with a living tissue is described above, however, another acoustic characteristic of the microbubble contrast agent when the contrast agent is compared with a living tissue is that irreversible change such as instability, disappearance, reduction and conjunction may be caused by the radiation of an ultrasonic pulse.

FIG. 4 shows another embodiment of the invention in case a pulse echo image is acquired by enhancing the distribution of a contrast agent utilizing such a property. One acoustic pressure waveform acquired by superimposing higher harmonics on a fundamental wave such as the examples shown in FIGS. 5 to 8 is selected and is transmitted in fixed amplitude plural times. To explain a case of transmitting twice as an example, a component that does not vary is eliminated by once recording a signal acquired by converging a received wave acquired by first transmission in the memory 9 and calculating difference between the recorded signal and a signal acquired by converging a received wave acquired by second transmission, and a temporal change component corresponding to the irreversible change of the contrast agent is extracted. When the difference is simply calculated, a signal from a stationary living tissue is completely eliminated and inconvenience may be caused when the distributional position of the contrast agent is displayed. This problem can be solved by not weighting a signal acquired by first transmission and a signal acquired by second transmission completely equally when the difference is calculated but increasing or decreasing weight by a few percents. Or the problem can-be solved by not making a time base completely coincident when the difference is calculated but shifting a few percents of the cycle of an ultrasonic wave. The processing described above is applied to a signal acquired by executing such signal processing in a temporal change component detector 11 to be a display signal.

FIGS. 5 to 8 show the results of measuring the acoustic pressure waveform of a transmitted wave when an ultrasonic wave is radiated in water using the ultrasonograph equivalent to the embodiment of the invention having the configuration shown in FIGS. 3 or 4 in the vicinity of the transducer array (the ultrasonic probe) by a needle like hydrophone. The hydrophone that can acquire voltage output proportional to input acoustic pressure and equal to the input acoustic pressure in a sign is used. For examples, four types of acoustic pressure waveforms acquired by shifting its phase when a second harmonic is superimposed on a fundamental wave, that is, the maximum positive-pressure enhanced waveform shown in FIG. 5, the maximum negative-pressure enhanced waveform shown in FIG. 6, the acoustic pressure rise enhanced waveform (N wave) shown in FIG. 7 and the acoustic pressure fall enhanced waveform (reverse N wave) shown in FIG. 8 are shown. Each amplitude of the fundamental wave component and the second harmonic component is fixed.

FIGS. 9 to 12 show the distribution of the size (the particle diameter) of a microbubble before and after ultrasonic waves having the acoustic pressure waveforms shown in FIGS. 5 to 8 are radiated on suspended microbubbles in water by fixed frequencies. FIGS. 9 to 12 show cases in which the maximum positive pressure enhanced waveform shown in FIG. 5, the maximum negative pressure enhanced waveform shown in FIG. 6, the acoustic pressure rise enhanced waveform shown in FIG. 7 and the acoustic pressure fall enhanced waveform shown in FIG. 8 are used for respective acoustic pressure waveforms. In FIGS. 9 to 12, a solid line (B) denotes a state before an ultrasonic wave is radiated, an alternate long and short dash line (C) denotes a state after an ultrasonic wave is radiated and a dotted line (D) denotes difference between the results of measurement before and after the ultrasonic wave is radiated.

In the case of any waveform, the number of microbubbles a few micron in a diameter resonated with an ultrasonic wave used in the ultrasonograph the frequency of which is approximately 2 MHz decreased. In the meantime, the number of microbubbles below 1 micron in a diameter slightly increases, however, this is considered because the agent that stabilized a destroyed microbubble is counted.

A further comparison of the results by the four types of waveforms shows that under a condition that the intensity of an ultrasonic wave is fixed, in the case of the acoustic pressure fall enhanced waveform (reverse N wave), microbubbles are eliminated particularly at high efficiency and conversely, in the case of the acoustic pressure rise enhanced waveform (N wave) and the maximum positive pressure enhanced waveform, the elimination of microbubbles is remarkably inhibited. The result of the experiment agrees well with the result of theoretical prediction by numerical calculation shown in FIG. 1.

As described above, when an image is obtained, keeping the stabilized microbubble contrast agent in a desired living area possibly, it is advantageous to select the acoustic pressure rise enhanced waveform, the maximum positive pressure enhanced waveform or an intermediate waveform and to acquire a pulse echo image emphasizing the distribution of the contrast agent by extracting a temporal change component by transmitting plural times or by extracting a nonlinear component by amplitude modulation.

Conversely, when an image is obtained, efficiently eliminating the stabilized microbubble contrast agent in a desired living area at as low ultrasonic energy as possible, it is advantageous to select the acoustic pressure fall enhanced waveform and to acquire a pulse echo image emphasizing the distribution of the contrast agent by extracting a temporal change component by transmitting plural times or by extracting a nonlinear component by amplitude modulation or pulse inversion.

Or when an image is obtained, efficiently eliminating the stabilized microbubble contrast agent in a living area by the radiation of an ultrasonic wave at as a low mechanical index as possible, it is advantageous to select the maximum positive pressure enhanced waveform and to acquire a pulse echo image emphasizing the distribution of the contrast agent by extracting a temporal change component by transmitting plural times or by extracting a nonlinear component by amplitude modulation.

It is considered that ultrasonic image diagnosis utilizing the characteristic of the stabilized microbubble contrast agent is enabled by suitably switching the contrast agent keeping image obtaining mode and the contrast agent eliminating imaging mode using the ultrasonograph having the configuration shown in FIG. 3 or 4 to which the invention is applied.

INDUSTRAIL AVAILABILITY

As described above, according to the invention, the ultrasonograph wherein ultrasonic image obtaining at satisfactory image signal-to-noise ratio and an enough frame rate is enabled, inhibiting the decrease of the density of the stabilized microbubble contrast agent in a desired living area by controlling the waveform of a transmitted wave and besides, the stabilized microbubble contrast agent in the desired living area can be efficiently eliminated if necessary, keeping the intensity of an ultrasonic wave and a mechanical index within a limit for safety can be realized. Therefore, the meaning in medical care and industry of the invention can be said to be large.

What is claimed is:

1. An ultrasonograph for obtaining an image of the inside of a living body by transmitting/receiving an ultrasonic wave to the living body into which a contrast agent is introduced comprising:
   an ultrasonic probe transmitting a first ultrasonic pulse and a second ultrasonic pulse, generated by superimposing higher harmonics including at least a second harmonic of a fundamental wave;
   a memory for recording a first converted signal acquired by converging the signal acquired by transmission of the first ultrasonic pulse; and
   a temporal change component detector for extracting a temporal change component corresponding to an irreversible change of the contrast agent caused by radiation of the ultrasonic pulse,
   wherein:
   the first ultrasonic pulse is an acoustic pressure rise enhanced waveform in which a leading edge of an ultrasonic acoustic pressure waveform is sharper than a trailing edge of the ultrasonic acoustic pressure waveform,
   the second ultrasonic pulse is an acoustic pressure fall enhanced waveform in which a trailing edge of an ultrasonic acoustic pressure waveform is sharper than a leading edge the ultrasonic acoustic pressure waveform,
   the ultrasonic probe transmits the first ultrasonic pulse or the second ultrasonic pulse with switching an ultrasonic acoustic pressure waveform,
   the temporal change component detector calculates a difference between the first converted signal recorded in the memory and a second converted signal acquired by converging the signal acquired by transmission of the second ultrasonic pulse as the temporal change component, and
   the temporal change component detector adds variable weight to the first converted signal and/or the second converted signal.

2. An ultrasonograph according to claim 1, wherein:
   an ultrasonic pulse transmitted from the ultrasonic probe includes a maximum positive pressure enhanced waveform in which the peak value on the side of positive acoustic pressure of maximum amplitude is larger than the peak value on the side of negative acoustic pressure.

3. An ultrasonograph according to claim 1, wherein: an ultrasonic pulse transmitted from the ultrasonic probe includes a maximum negative pressure enhanced waveform in which the peak value of the side of negative acoustic pressure of maximum amplitude is larger than the peak value on the side of positive acoustic pressure.

4. An ultrasonograph according to claim 1, wherein: the contrast agent includes microbubbles; and
   the mean frequency of the fundamental wave is set to the resonance frequency of the microbubble at the mean diameter of microbubbles introduced.

5. An ultrasonograph according to claim 1, wherein:
   the ultrasonic pulse has a waveform generated by superimposing a second harmonic the phase of which is shifted by $\pi/2$ at a point that crosses zero from the fundamental wave on the fundamental wave.

6. An ultrasonograph according to claim 1, wherein:
   the ultrasonic pulse has a waveform generated by superimposing a second harmonic the phase of which is equal to that of the fundamental wave at a point that crosses zero on the fundamental wave.

7. An ultrasonic apparatus for obtaining an image of the inside of a living body by transmitting/receiving an ultrasonic wave to the living body into which a contrast agent is introduced comprising:
   an ultrasonic probe transmitting a first ultrasonic pulse and a second ultrasonic pulse, generated by superimposing higher harmonics including at least a second harmonic of fundamental wave on the fundamental wave
   a memory for recording a first converted signal acquired by converging the signal acquired by transmission of the first ultrasonic pulse; and temporal change component detector extracting a temporal change component corresponding to the irreversible change of the contrast agent caused by radiation of the ultrasonic pulse, wherein:
- an ultrasonic pulse transmitted from the ultrasonic probe includes a maximum positive pressure enhanced waveform in which the peak value on the side positive acoustic pressure of maximum amplitude is larger than the peak value on the side of negative acoustic pressure,
- an ultrasonic pulse transmitted from the ultrasonic probe includes a maximum negative pressure enhanced waveform in which the peak value on the side of negative acoustic pressure of maximum amplitude is larger than the peak value on the side of positive acoustic pressure,
- the ultrasonic proved transmit the first ultrasonic pulse or the second ultrasonic pulse with switching an ultrasonic acoustic pressure waveform
- the temporal change component detector calculates a difference between the first converted signal recorded in the memory and a second converted signal acquired by converging the signal acquired by transmission of the second ultrasonic pulse as the temporal change component; and
- the temporal change component detector adds variable weight to the first converted signal and/or the second converted signal.

* * * * *